United States Patent [19]
Kun et al.

[11] Patent Number: 5,736,576
[45] Date of Patent: Apr. 7, 1998

[54] METHOD OF TREATING MALIGNANT TUMORS WITH THYROXINE ANALOGUES HAVING NO SIGNIFICANT HORMONAL ACTIVITY

[75] Inventors: Ernest Kun, Mill Valley; Jerome Mendeleyev, Tiburon, both of Calif.

[73] Assignee: Octamer, Inc., Mill Valley, Calif.

[21] Appl. No.: 655,267

[22] Filed: Jun. 4, 1996

[51] Int. Cl.$^6$ .............................. A61K 31/19; C07C 69/76
[52] U.S. Cl. .......................... 514/570; 514/568; 560/59; 560/60; 560/61; 560/62
[58] Field of Search .................................. 514/568, 570; 560/59, 60, 61, 62

[56] References Cited

U.S. PATENT DOCUMENTS

| | | | |
|---|---|---|---|
| 4,724,234 | 2/1988 | Cone | 514/728 |
| 4,816,255 | 3/1989 | Ghent | 424/150 |

FOREIGN PATENT DOCUMENTS

| | | |
|---|---|---|
| 642159 | 8/1950 | United Kingdom . |
| 643089 | 9/1950 | United Kingdom . |
| WO-93/2442 | 12/1993 | WIPO . |

OTHER PUBLICATIONS

Borrows and Clayton, 1951, *Chem. Abstr.* 45:P7594b.
Borrows et al., 1950, *Chem. Abstr.* 44:574h.
Borrows et al., 1949, "The Synthesis of Thyroxine and Related Substances. Part I. The Preparation of Tyrosine and Some of its Derivatives, and a New Route to Thyroxine," 1949, *J. Chem. Soc.* 1949 (Supp. Issue No. 1): S185–S190.
Borrows et al., 1949, "The Synthesis of Thyroxine and Related Substances. Part II. The Preparation of Dinitrodiphenyl Ethers," 1949, *J. Chem. Soc.* (Supp. Issue No. 1): S190–S199.
Clayton et al., 1952, *Chem. Abstr.* 46:8056g.
Clayton et al., 1951, "The Synthesis of Thyroxine and Related Substances. Part VIII. The Preparation of Some Halogeno–and Nitro–diphenyl Ethers," *J. Am. Chem. Soc.* 1951:2467–2473.
Crowder et al., 1958, *Chem. Abstr.* 52:17163d.
Crowder et al., 1958, "Bisbenzylisoquinolines. Part II. the Synthesis of 5–(2–Aminoethyl)–4'–carboxy–2, 3–dimethoxydiphenyl Ether," *J. Chem. Soc.* 1958:2142–2149.

Dunphy, 1994, *Trends Cell. Biol.* 4:202–207.
Grinberg et al., 1962, *Chem. Abstr.* 57:14335d.
Grinberg et al., 1962, "Studies with Mouse Pituitary Thyrotropic Tumors. V. Effect of Various Thyroxine Analogs on Growth and Secretion," *Cancer Research* 22:835–841.
Jorgensen, 1978, "Thyroid Hormones and Analogues, II. Structure Activity Relationships," In: *Hormonal Proteins and Peptides* 108–203 (C.H. Li, Ed.).
Kumaoka et al., 1960, *Chem. Abstr.* 54:18779i.
Kumaoka et al., 1960, "The Effect of Thyroxine Analogues on a Transplantable Mouse Pituitary Tumor," *Endocrinology* 66:32–38.
Masuda et al., 1971, *Chem. Abstr.* 75:140431q.
Masuda et al., 1970, "Thyroxine Related Compounds. I. Synthesis of Triiodothyroformic Acid and its Derivatives," *Takeda Kenkyusho Ho* 29(4):545–552 (in Japanese).
Meltzer et al., 1958, *Chem. Abstr.* 52:7210d.
Meltzer et al., 1957, "Thyroxine Analogs," *J. Org. Chem.* 22:1577–1581.
Money et al., 1958, *Chem. Abstr.* 52:20701a.
Money et al., 1958, "The Effect of Change in Chemical Structure of Some Thyroxine Analogues on the Metamorphosis of *Rana Pipiens* Tadpoles," *Endocrinology* 63:20–28.
Money et al., 1959, *Chem. Abstr.* 53:14327i.
Money et al., 1959, "The Effect of Various Thyroxine Analogues on Suppression of Iodine–131 Uptake by the Rat Thyroid," *Endocrinology* 64:123–125.
Stasilli et al., 1959, *Chem. Abstr.* 53:14327ci.
Stasilli et al., 1959, "Antigoitrogenic and Calorigenic Activities of Thyroxine Analogues in Rats," *Endocrinology* 64:62–82.
Tomita et al. "Synthesis and biological activity of some triiodinated analogues of thyroxine" *J. Biol. Chem.* v. 219, pp. 595–604, 1956.
Grutzmeier S. "Myxoedema in a case of acute myoloid leukemia" EMBASE 85:118288, 1985.
Dykes et al. "Response of human tumor xenografts in athymic nude mice . . . " BIOSIS 95:487870, 1995.

*Primary Examiner*—Ceila Chang
*Attorney, Agent, or Firm*—Albert P. Halluin; Howrey & Simon

[57] ABSTRACT

The present invention provides methods for treating cancer, particularly malignant tumors, with thyroxine analogues having no significant hormonal activity. A thyroxine analogue is administered to an afflicted mammal in an amount effective to cause depression or regression of malignant tumor growth or to treat cancer.

3 Claims, No Drawings

METHOD OF TREATING MALIGNANT TUMORS WITH THYROXINE ANALOGUES HAVING NO SIGNIFICANT HORMONAL ACTIVITY

FIELD OF THE INVENTION

The present invention relates generally to the field of cancer therapeutics. More specifically, the present invention relates to the use of thyroxine analogues having no significant hormonal activity, particularly methyl 3,5-diiodo-4-(4'-methoxyphenoxy)benzoate, as potent, selective and non-toxic anti-tumor agents.

BACKGROUND OF THE INVENTION

Cancer is a serious threat to modern society. Malignant cancerous growths, due to their unique characteristics, pose serious challenges for modern medicine. These characteristics include uncontrollable cell proliferation resulting in unregulated growth of malignant tissue, an ability to invade local and even remote tissues, lack of differentiation, lack of detectable symptoms and most significantly, the lack of effective therapy and prevention.

Cancer can develop in any tissue of any organ at any age. The etiology of cancer is not clearly defined but mechanisms such as genetic susceptibility, chromosome breakage disorders, viruses, environmental factors and immunologic disorders have all been linked to a malignant cell growth and transformation.

Antineoplastic chemotherapy currently encompasses several groups of drugs including alkylating agents, purine antagonists and antitumor antibiotics. Alkylating agents alkylate cell proteins and nucleic acids preventing cell replication, disrupting cellular metabolism and eventually leading to cell death. Typical alkylating agents are nitrogen mustard, cyclophosphamide and chlorambucil. Toxicities associated with alkylating agents treatment include nausea, vomiting, alopecia, hemorrhagic cystitis, pulmonary fibrosis and an increased risk of developing acute leukemia.

Purine, pyrimidine and folate antagonists are cell cycle and phase specific and, in order to promote an antitumor effect, they require cells to be in the cell replication cycle and in the DNA synthesis phase of replication. The purine antagonists such as 6-mercaptopurine or 6-thioguanidine inhibit de novo purine synthesis and interconversion of purines. The pyrimidine antagonists, such as cytarabine, 5-fluorouracil or floxuridine inhibit DNA synthesis by inhibiting deoxycytidylate kinase and DNA polymerase.

Folate antagonists, e.g., methotrexates, bind tightly with the intracellular enzyme dihydrofolate reductase ultimately leading to cell death resulting from an inability to synthesize pyrimidines. Toxicities associated with the use of these compounds include alopecia, myelosuppression, vomiting, nausea, and cerebellar ataxia, among others.

Plant alkaloids such as vincristine, vinblastine or podophyllotoxins etoposide and teniposide generally inhibit mitosis and DNA synthesis and RNA dependent protein synthesis. Toxicities of these drugs are similar to those described above and include myopathy, myelosuppression, peripheral neuropathy, vomiting, nausea and alopecia.

Antitumor antibiotics such as doxorubicin, daunorubicin and actinomycin act as intercalators of DNA, preventing cell replication, inhibiting synthesis of DNA-dependent RNA and inhibiting DNA polymerase. Bleomycin causes scission of DNA and mitomycin acts as inhibitor of DNA synthesis by bifunctional alkylation. Toxicities of these antibiotics are numerous and severe and include necrosis, myelosuppression, anaphylactic reactions, anorexia, dose-dependent cardiotoxicity and pulmonary fibrosis.

Other compounds used for chemotherapeutical treatment of cancer are inorganic ions such as cisplatin, biologic response modifiers such as interferon, enzymes and hormones. All these compounds, similarly to those mentioned above, are accompanied by toxic adverse reactions.

Accordingly, it would be extremely advantageous to provide safe and non-toxic chemotherapeutic compositions which would effectively inhibit and/or suppress tumor cell proliferation and/or neoplastic growth. Furthermore, it would be extremely advantageous to provide safe, effective and non-toxic chemotherapeutic compositions that are easy to administer.

The identification of safe, effective, non-toxic, and orally administrable organic compounds capable of depressing or regressing malignant tumor growth in mammals and the use of such compounds to treat cancer is therefore desirable and the object of this invention.

SUMMARY OF THE INVENTION

The present invention relates to the use of thyroxine analogues having no significant hormonal activity, particularly methyl 3,5-diiodo-4-(4'-methoxy phenoxy)benzoate ("DIME") to depress or regress malignant tumor growth and to treat cancer. The method generally involves administering to a mammal an amount of a thyroxine analogue effective to depress or regress malignant tumor growth or to treat cancer. The thyroxine analogues typically are characterized as lacking significant hormonal activity.

In one illustrative embodiment, thyroxine analogues useful in the methods of the present invention are compounds having the structural formula:

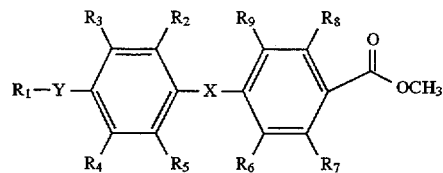

and pharmaceutically acceptable salts thereof, wherein:

X=O, S, $CH_2$, carboxy or absent;

Y=O or S;

$R_1$=methyl or ethyl;

$R_2$, $R_3$, $R_4$ and $R_5$ are each independently selected from the group consisting of: H, ($C_1$–$C_4$) alkyl, ($C_1$–$C_4$) alkenyl, ($C_1$–$C_4$) alkynyl, hydroxy, ($C_1$–$C_4$) alkoxy and halogen; and $R_6$, $R_7$, $R_8$ and $R_9$ are each independently selected from the group consisting of: H, ($C_1$–$C_4$) alkyl, ($C_1$–$C_4$) alkenyl, ($C_1$–$C_4$) alkynyl, hydroxy, ($C_1$–$C_4$) alkoxy, halogen, $NO_2$ and $NH_2$.

In another illustrative embodiment, thyroxine analogues useful in the methods of the present invention are compounds having the structural formula:

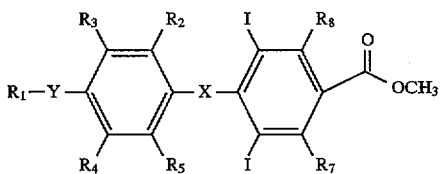

and pharmaceutically acceptable salts thereof, wherein:

X=O, S, CH$_2$, carboxy or absent;

Y=O or S;

R$_1$=methyl or ethyl;

R$_2$, R$_3$, R$_4$ and R$_5$ are each independently selected from the group consisting of: H, (C$_1$-C$_4$) alkyl, (C$_1$-C$_4$) alkenyl, (C$_1$-C$_4$) alkynyl, hydroxy, (C$_1$-C$_4$) alkoxy and halogen; and R$_7$ and R$_8$ are each independently selected from the group consisting of: H, (C$_1$-C$_4$) alkyl, (C$_1$-C$_4$) alkenyl, (C$_1$-C$_4$) alkynyl, hydroxy, (C$_1$-C$_4$) alkoxy, halogen, NO$_2$ and NH$_2$.

In a preferred embodiment of the invention the thyroxine analogue is methyl 3,5-diiodo-4-(4'-methoxyphenoxy) benzoate ("DIME") .

BRIEF DESCRIPTION OF THE FIGURES

FIG. 1 is a photograph demonstrating the morphologic action of DIME on E-ras transformed bovine endothelial cells;

FIG. 2 is a graph illustrating the loss of tumorigenicity of DIME-treated E-ras transformed bovine endothelial cells; and FIG. 3 is a graph illustrating the serum half-life ($t_{1/2}$) and the oral bioavailability of DIME in mice.

DETAILED DESCRIPTION OF THE INVENTION

Definitions

As used herein:

"Alkyl" refers to a saturated branched, straight chain or cyclic hydrocarbon radical. Typical alkyl groups include methyl, ethyl, propyl, isopropyl, cyclopropyl, butyl, isobutyl, cyclobutyl, tert-butyl, pentyl, hexyl and the like.

"Alkenyl" refers to an unsaturated branched, straight chain or cyclic hydrocarbon radical having at least one carbon-carbon double bond. The radical may be in either the cis or trans conformation about the double bond(s). Typical alkenyl groups include ethenyl, propenyl, isopropenyl, cyclopropenyl, butenyl, isobutenyl, cyclobutenyl, tert-butenyl, pentenyl, hexenyl and the like.

"Alkynyl" refers to an unsaturated branched, straight chain or cyclic hydrocarbon radical having at least one carbon-carbon triple bond. Typical alkynyl groups include ethynyl, propynyl, butynyl, isobutynyl, pentynyl, hexynyl and the like.

"Alkoxy" refers to an —OR radical, where R is alkyl, alkenyl or alkynyl, as defined above.

"Halogen" refers to fluoro, chloro, bromo and iodo substituents.

"Mammal" refers to animals or humans.

"Pharmaceutically acceptable salt" refers to those salts of compounds which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutically acceptable salts include, for example, alkali metal salts such as sodium and potassium, alkaline earth salts and ammonium salts.

"Pharmacophore" refers to the critical three-dimensional arrangement of molecular moieties or fragments (or the distribution of electron density) that is recognized by a receptor (*Burger's Medicinal Chemistry and Drug Delivry Vol. I: Principles and Practice* 619, 5th Edition, John Wiley & Sons, New York).

"Therapeutically effective amount" refers to an amount of a compound or composition effective to depress, suppress or regress malignant cell growth or result in amelioration of symptoms associated with cancerous diseases.

Description of Specific Embodiments

The present invention relates to methods of treating malignant tumors and cancer in mammals with analogues of thyroxine which are characterized as having no significant hormonal activity. Preferably, the present invention is based, in part, on the surprising discovery that certain analogues of thyroxine that do not exhibit hormonal activity are potent, selective and non-toxic inhibitors of malignant tumor growth. The preferred thyroxine analogue is referred to herein as DIME.

Thyroxine, an amino acid of the thyroid gland (Merck Index, 1989, 9348:1483) and thyroxine analogues are well-known in the art. It is well established in the literature that thyroid hormones, specifically thyroxines T3 and T4, have two distinct types of biological actions: one on cell metabolism, the second on cell differentiation and development (Jorgensen, 1978, "Thyroid Hormones and Analogues II. Structure-Activity Relationships," In: *Hormonal Proteins and Peptides*, Vol. VI, pp. 107–204, C. H. Li, ed., Academic Press, NY). For example, thyroxine suppresses uptake of iodine by the thyroid (Money et al., 1959, "The Effect of Various Thyroxine Analogues on Suppression of Iodine-131 Uptake by the Rat Thyroid," *Endocrinology* 64:123–125) and induces cell differentiation as studied by tadpole metamorphosis (Money et al., 1958, "The Effect of Change in Chemical Structure of Some Thyroxine Analogues on the Metamorphosis of Rana Pipiens Tadpoles," *Endocrinology* 63:20–28). Additionally, thyroxine and certain thyroxine analogues depress growth of non-malignant mouse pituitary thyrotropic tumors (Kumaoka et al., 1960, "The Effect of Thyroxine Analogues on a Transplantable Mouse Pituitary Tumor," Endocrinology 66:32–38; Grinberg et al., 1962, "Studies with Mouse Pituitary Thyrotropic Tumors. V. Effect of Various Thyroxine Analogs on Growth and Secretion," *Cancer Research* 22:835–841).

The structural requirements of thyroxine and thyroxine analogues for metabolic stimulation and induction of cell differentiation are not identical (see Jorgensen, 1978, "Thyroid Hormones and Analogues II. Structure-Activity Relationships," In: *Hormonal Proteins and Peptides*, Vol. VI, p. 150, C. H. Li, ed., Academic Press, NY). For example, Money et al. have found that there is no correlation between suppression of thyroid iodine uptake and induction of tadpole metamorphosis (Money et al., 1958, "The Effect of Change in Chemical Structure of Some Thyroxine Analogues on the Metamorphosis of Rana Pipiens Tadpoles," *Endocrinology* 63:20–28).

Based on these observations, it was conceived that as yet unidentified cellular responses may be altered or induced by certain thyroxine analogues which do not exhibit either mode of action (metabolic or differentiating) exhibited by thyroxine T3 and T4.

The Compounds

Thyroxine analogues useful in the methods of the present invention are generally compounds having the structural formula:

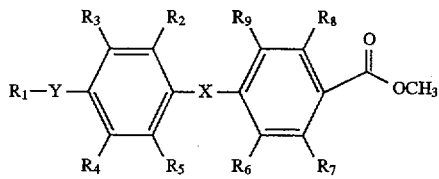

and pharmaceutically acceptable salts thereof, wherein:

X=O, S, $CH_2$, carboxy or absent;
Y=O or S;
$R_1$=methyl or ethyl;
$R_2$, $R_3$, $R_4$ and $R_5$ are each independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy and halogen; and
$R_6$, $R_7$, $R_8$ and $R_9$ are each independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy, halogen, $NO_2$ and $NH_2$.

In a preferred embodiment, thyroxine analogues useful in the methods of the present invention are compounds having the structural formula:

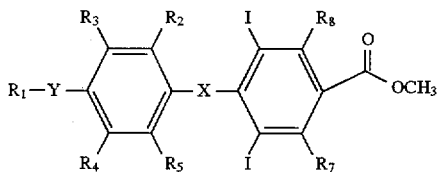

and pharmaceutically acceptable salts thereof, wherein:

X=O, S, $CH_2$, carboxy or absent;
Y=O or S;
$R_1$=methyl or ethyl;
$R_2$, $R_3$, $R_4$ and $R_5$ are each independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy and halogen; and
$R_7$ and $R_8$ are each independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy, halogen, $NO_2$ and $NH_2$.

In a particularly preferred embodiment, the thyroxine analogue is methyl 3,5-diiodo-4-(4'-methoxyphenoxy) benzoate ("DIME").

Thyroxine analogues such as DIME have been described in the literature. However, unlike thyroxine, DIME was reported to have no significant metabolic or cell differentiating activity (as determined by tadpole metamorphosis) (Money et al., 1958, "The Effect of Change in Chemical Structure of Some Thyroxine Analogues on the Metamorphosis of Rana Pipiens Tadpoles," *Endocrinology* 3:20–28; Stasilli et al., 1959, "Antigoitrogenic and Calorigenic Activities of Thyroxine Analogues in Rats," *Endocrinology* 64:62–82). For example, uptake of iodine into the thyroid of rats is only marginally (15%) inhibited by DIME as compared to thyroxine (Money et al., 1959, "The Effect of Various Thyroxine Analogues on Suppression of Iodine-131 Uptake by the Rat Thyroid," *Endocrinology* 64:123–125). Furthermore, DIME was reported to have no inhibitory activity against the growth of a non-malignant mouse pituitary adenoma (Kumaoka et al., 1960, "The Effect of Thyroxine Analogues on a Transplantable Mouse Pituitary Tumor," *Endocrinology* 66:32–38; Grinberg et al., 1962, "Studies with Mouse Pituitary Thyrotropic Tumors. V. Effect of Various Thyroxine Analogs on Growth and Secretion," *Cancer Research* 22:835–841). No studies with malignant cells have been reported.

It has now been discovered that certain thyroxine analogues having no significant hormonal activity, particularly DIME, not only inhibit the growth of a variety of malignant cell types (see Table 3), but induce tumor cell apoptosis preceded by micronucleation as well. These cytostatic and cytocidal activities are sensitive to structure. Testing of thirteen structural analogues and homologues of DIME indicates that even minor alterations of the methyl ester and 4'-methyoxy substituents renders the molecule completely inactive. Whereas DIME is highly active both in cellular assays and in vivo, the 4'-propoxy and ethyl ester homologues are completely inactive. Accordingly, DIME defines a critical arrangement of molecular moieties, or a pharmacophore, having specific cytostatic and cytocidal activity, and consequently significant chemotherapeutic potential.

While not intending to be bound by theory, it is believed that the most probable molecular mode of action of the thyroxine analogues described herein is cell cycle inhibition and induction of apoptosis.

Progression of eukaryotic cells through the cell division cycle is primarily controlled by the activity of cyclin-dependent protein kinases. The best studied event is the transition from G2 to M phase, which is controlled by cdc2 kinase complexed with cyclin B (for a review see, Dunphy, 1994, *Trends Cell. Biol.* 4:202–207). cdc2 kinase activation requires phosphorylation, a process that is regulated by protein phosphatase 2A (for a review, see, Wera & Hennings, 1995, *Biochem. J.* 311:17–29).

It has been discovered that the thyroxine analogues described herein exert specific activation of protein phosphatase 2A both in vitro and in vivo. In vivo, activation of protein phosphatase 2A coincides with inhibition of cdc2 kinase and dephosphorylation of MAP kinase and topoisomerase II, rendering both of the latter enzymes inactive. DIME has no metabolic action, nor does it inhibit the biosynthetic pathways of DNA, RNA or proteins. Thus, the most probable mode of action is cell cycle inhibition and induction of apoptosis via dephosphorylation of these critical regulatory proteins. Accordingly, activation of phosphatase 2A and concomitant inhibition of cdc2 kinase is an important and powerful therapeutic target for the treatment of cancer.

While alterations at the ester and 4'-positions appear to significantly affect the effectivity of DIME, thyroxine analogues useful for depressing malignant tumor growth and treating cancer are not limited to DIME. For example, the 4'-ethoxy homologue exhibits about 25–30% maximal cytocidal action on human cancer cells as compared to DIME (Example 4). It is also expected that DIME may be substituted at the aromatic ring positions or bridge oxygen without significant loss of activity.

It is known that the aromatic rings of thyroxine are not contained within the same plane (Jorgensen, 1978, "Thyroid Hormones and Analogues II. Structure-Activity Relationships," In: *Hormonal Proteins and Peptides*, Vol. VI, pp. 107–204, C. H. Li, ed., Academic Press, NY). It is also known that the ring positions of both of the aromatic rings in thyroxine can be substituted with a variety of substituents, including alkyl, halogen, nitro and amino groups with varying degrees of retention of hormonal activity (ibid). Furthermore, the ether oxygen connecting the rings can be absent or replaced with a variety of groups or atoms that do not confine the aromatic rings to the same plane, such as, for example, a methylene group, a carboxy group or sulfur, without significant loss of hormonal activity (ibid). Accordingly, it is expected and predictable that similar substitutions on DIME will not effect significant loss of anti-cancer activity. Significantly, the 2'-chloro analogue of DIME exhibited about 25% maximal inhibitory action on the growth of human cancer cells as compared to DIME (Example 5).

Due to the stringent correlation between in vitro and in vivo efficacy (see, Examples 2–7), effective compounds useful in the methods of the invention may be conveniently identified in in vitro assay screening tests. Such tests may screen for the ability of a particular compound to activate protein phosphatase 2A, as described in Examples 2–3. Typically, compounds useful in the methods of the present invention will increase protein phosphatase 2A activity by a factor of about two to three, as measured by the assay described in Example 2 or 3.

Such tests may also screen for the ability of a particular compound to inhibit malignant tumor cell growth in vitro or in vivo or abolish tumorigenicity of malignant cells, as described in Examples 4–6. Generally, active compounds useful in the methods of the present invention will exhibit an $I_{50}$ (concentration of compound lethal to 50% of a cell culture as compared to a control culture) in the range of about 0.5 μm to 5.0 μm, as measured by the assay described in Example 4.

As will be appreciated by the skilled artisan, many varieties of malignant tumor cell cultures and cell lines may be used to screen for activity, including but not limited to HL-60, HT-144, E-ras-20, DU-145, MDA-168, MCF-7, 855-2 and MDA-MB-231. Of course, other in vitro and/or in vivo assays as will be apparent to the skilled artisan to screen for anti-tumor and/or anti-cancer activity may also be employed to identify effective thyroxine analogues useful in the present invention.

The chemical formulae referred to herein may exhibit the phenomena of tautomerism or conformational isomerism. As the formulae drawings within this specification can only represent one of the possible tautomeric or conformational isomeric forms, it should be understood that the invention encompasses any tautomeric or conformational isomeric forms which exhibit biological or pharmacological activities similar to DIME, as described herein.

In addition to the above-described compounds and their pharmaceutically acceptable salts, the invention may employ, where applicable, solvated as well as unsolvated forms of the compounds (e.g. hydrated forms).

The compounds described herein may be prepared by any process known to be applicable to the preparation of chemical compounds. Suitable processes are illustrated by the representative examples. Necessary starting materials may be obtained by standard procedures of organic chemistry.

Cancers

The thyroxine analogues described herein are useful for treating a wide variety of cancers. Such cancers include, by way of example and not limitation, carcinomas such as pharynx, colon, rectal, pancreatic, stomach, liver, lung, breast, skin, prostate, ovary, cervical, uterine and bladder cancers; leukemias; lymphomas; gliomas; retinoblastomas; and sarcomas.

In a preferred embodiment of the invention, the cancer is associated with the formation of solid tumors including, by way of example and not limitation, mammary and prostatic cancers.

Pharmaceutical Formulations And Routes Of Administration

A thyroxine analogue useful in the present invention can be administered to a human patient per se, in the form of a pharmaceutically acceptable salt, or in the form of a pharmaceutical composition where the compound is mixed with suitable carriers or excipient(s) in a therapeutically effective amount, i.e., at doses effective to depress or suppress malignant cell growth or result in amelioration of symptoms associated with cancerous diseases.

Routes Of Administration

The thyroxine analogues and pharmaceutical compositions described herein may be administered by a variety of routes. Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than systemic manner, for example via injection of the compound directly into a solid tumor, often in a depot or sustained release formulation.

Furthermore, one may administer the compound in a targeted drug delivery system, for example, in a liposome coated with tumor-specific antibody. The liposomes will be targeted to and taken up selectively by the tumor.

In a preferred embodiment, the thyroxine analogues and pharmaceutical compositions described herein are administered orally.

Composition/Formulation

The pharmaceutical compositions described herein may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining with pharmaceutically acceptable carriers that are well known in the art. Such carriers enable the compounds to be formulated as tablets, pills, dragees, capsules, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A suitable pharmaceutical carrier for hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% (w/v) benzyl alcohol, 8% (w/v) of the nonpolar surfactant polysorbate 80, and 65% (w/v) polyethylene glycol 300, made up to volume in absolute ethanol. The VPD co-solvent system (VPD:5W) consists of VPD diluted 1:1 with a 5% (w/v) dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Other formulations suitable for administering the thyroxine analogues described herein will be apparent to those having skill in the art, and may be found, for example, in *Remington's Pharmaceutical Sciences*, Mack Publishing Co., Easton, Pa., latest edition.

Effective Dosages

Pharmaceutical compositions suitable for use in the present invention include compositions wherein the active ingredients are contained in a therapeutically effective amount. Determination of an effective amount is well within the capability of those skilled in the art, especially in light of the detailed disclosure provided herein.

For any compound used in the method of the invention, a therapeutically effective dose can be estimated initially from cell culture assays. For example, a dose can be formulated in animal models to achieve a circulating concentration range that includes the $I_{50}$ as determined in cell culture (i.e., the concentration of test compound that is lethal to 50% of a cell culture) or the $I_{100}$ as determined in cell culture (i.e., the concentration of compound that is lethal to 100% of a cell culture). Such information can be used to more accurately determine useful doses in humans.

Initial dosages can also be estimated from in vivo data. For example, it has been found that 250 mg/kg administered by gavage once daily, 5 days a week for 32 days significantly depressed the growth of mammary cancer xenografts (MDA-MB-231) in nude mice (see Example 7.3). Studies have also shown that DIME has a half-life ($t_{1/2}$) in serum of about 2–2.5 hours, and is 87% bioavailable by per os administration (see Example 7.2). One having ordinary skill in the art could readily optimize administration to humans based on this data.

Dosage amount and interval may be adjusted individually to provide plasma levels of the active compound which are sufficient to maintain therapeutic effect. Usual patient dosages for oral administration range from about 50–2000 mg/kg/day, commonly from about 250–1000 mg/kg/day, preferably from about 500–700 mg/kg/day and most preferably from about 350–550 mg/kg/day. Preferably, therapeutically effective serum levels will be achieved by administering multiple doses each day.

In cases of local administration or selective uptake, the effective local concentration of the drug may not be related to plasma concentration. One having skill in the art will be able to optimize therapeutically effective local dosages without undue experimentation.

The amount of composition administered will, of course, be dependent on the subject being treated, on the subject's weight, the severity of the affliction, the manner of administration and the judgment of the prescribing physician.

The chemotherapy may be repeated intermittently while tumors are detectable or even when they are not detectable. Moreover, due to its apparent nontoxicity (discussed below), the therapy may be provided alone or in combination with other anti-cancer or other drugs, such as for example AZT, anti-inflammatories, antibiotics, corticosteroids, vitamins and the like.

Possible synergism between the thyroxine analogues described herein and other drugs is expected and predictable. In addition, possible synergism between a plurality of thyroxine analogues is also expected and predictable.

and can be expressed as the ratio between $LD_{50}$ and $ED_{50}$. Compounds which exhibit high therapeutic indices are preferred. The data obtained from these cell culture assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics*, Ch.1, p.1).

One of the advantages, among others, of using the thyroxine analogues described herein to treat cancer is their lack of toxicity. For example, it has been found that a daily oral dose of 1 g/kg administered for 12–15 days produced no ill effects in nude mice (see Example 7.1). Since the i.v. serum half-life ($t_{1/2}$) of DIME is about 2–2.5 hours, repeated daily dosages of the thyroxine analogues described herein without ill effects is predictable.

The invention having been described, the following examples are offered to illustrate the subject invention by way of example, not by way of limitation.

EXAMPLE 1

COMPOUND SYNTHESES

Fourteen thyroxine analogues were synthesized, purified and characterized. A summary of the structure of each synthesized compound and select physical data is provided at Table 1, below.

TABLE 1

Thyroxine Analogues Synthesized

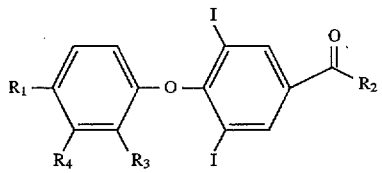

| No. | $R_1$ | $R_2$ | $R_3$ | $R_4$ | m.p.(°C.) | Formula | Mass (calcd.) | Mass (found) |
|---|---|---|---|---|---|---|---|---|
| 1 | $CH_3O$ | $CH_3O$ | H | H | 153–155 | $C_{15}H_{12}I_2O_4$ | 509.882513 | 509.882960 |
| 2 | EtO | $CH_3O$ | H | H | 123–125 | $C_{16}H_{14}I_2O_4$ | 523.898163 | 523.898737 |
| 3 | n-PrO | $CH_3O$ | H | H | 114–116 | $C_{17}H_{16}I_2O_4$ | 537.913813 | 537.914014 |
| 4 | n-BuO | $CH_3O$ | H | H | 82–84 | $C_{18}H_{18}I_2O_4$ | 551.929463 | 551.930000 |
| 5 | $CH_3O$ | EtO | H | H | 96–98 | $C_{16}H_{14}I_2O_4$ | 523.898163 | 523.898202 |
| 6 | $CH_3O$ | HO | H | H | 233–235 | $C_{14}H_{10}I_2O_4$ | ref$^a$ | |
| 7 | $CH_3O$ | $H_2N$ | H | H | 207–209 | $C_{14}H_{11}I_2NO_3$ | 494.882847 | 494.881880 |
| 8 | $CH_3O$ | $(CH_3)HN$ | H | H | 181–183 | $C_{15}H_{13}I_2NO_3$ | 508.898497 | 508.898971 |
| 9 | $CH_3O$ | $(CH_3)_2N$ | H | H | 162–164 | $C_{15}H_{13}I_2NO_3$ | 522.914148 | 522.914364 |
| 10 | HO | $CH_3O$ | H | H | 204 (dec.)$^b$ | $C_{14}H_{10}I_2O_4$ | 495.866863 | 495.867453 |
| 11 | H | $CH_3O$ | H | H | 142–144 | $C_{14}H_{10}I_2O_3$ | 479.871948 | 479.872553 |
| 12 | I | $CH_3O$ | H | H | 139–141 | $C_{14}H_9I_3O_3$ | 605.768600 | 605.767839 |
| 13 | H | $CH_3O$ | H | $CH_3O$ | 123–125 | $C_{15}H_{12}I_2O_4$ | 509.882513 | 509.882387 |
| 14 | $CH_3O$ | $CH_3O$ | Cl | H | 132–134 | $C_{15}H_{11}ClI_2O_4$ | 543.843541 | 543.843424 | ref$^a$: Compound 6 was prepared according to Borrows et al., J. Chem. Soc. 1949:S185–S190.
$^b$: Decomposition temperature.

Toxicity

Toxicity and therapeutic efficacy of the thyroxine analogues described herein can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio between toxic and therapeutic effect is the therapeutic index

1.1 Methyl 3,5-diiodo-4-(4'-methoxyphenoxy) benzoate (Compound 1)

Methyl 3,5-diiodo-4-(4'-methoxyphenoxy)benzoate (Compound 1) was prepared as described in Borrows et al., 1949, "The Synthesis of Thyroxine and Related Substances. Part I. The Preparation of Tyrosine and Some of its Derivatives, and a New Route to Thyroxine," *J. Chem. Soc.*

1949 (Supp. Issue No. 1):S185–S190, and recrystallized from 95% ethanol. Melting point: 153°–155° C.

Mass spectrum: FAB, m/z (relative intensity): 510 (M+, 100), 479 (4.5), 384 (4.5). High-resolution data for the M+ peak: calculated for $C_{15}H_{12}I_2O_4$, 509.882513; found, 509.882960 (deviation=−0.9 ppm).

$^1$H NMR spectrum in DMSO-d$_6$(δ(ppm) values relative to TMS): 3.719 (3H, singlet), 3.876 (3H, singlet), 6.693 (2H, doublet, J=9.45 Hz, plus fine-splitting), 6.845 (2H, doublet, H=9.36 Hz, plus fine-splitting), 8.390 (2H, singlet).

1.2 Methyl 3,5-diiodo-4-(4'-ethoxyphenoxy) benzoate (Compound 2)

Methyl 3,5-diiodo-4-(4'-ethoxyphenoxy)benzoate (Compound 2) was synthesized using the general methodology of Borrows, et al., 1949, "The Synthesis of Thyroxine and Related Substances. Part I. The Preparation of Tyrosine and Some of its Derivatives, and a New Route to Thyroxine," *J. Chem. Soc.* 1949 (Supp. Issue No. 1):S185–S190.

1.2.1 Methyl 3,5-dinitro-4-(4'-ethoxyphenoxy) benzoate

In a 50-ml flask at ambient temperature 4-ethoxy-phenol (Aldrich) (1492 mg, 10.8 mmoles) was stirred with 2.0M aqueous KOH (5.50 ml) to form potassium 4-ethoxy-phenolate. Methyl 4-chloro-3,5-dinitrobenzoate (Ullmann, 1909, *Annalen der Chemie* 366:92–93; commercial source: Spectrum Chemical Company, Gardena, Calif.; 2606 mg, 10.0 mmoles) was added, the mixture heated to reflux for 1 hour and chilled in an ice-bath, whereupon a rubbery mass of product deposited. Cold aqueous 1.0M KOH (20 ml) was added, and upon continued chilling the product solidified. The yellow-orange solid was broken-up, collected on a suction filter, rinsed with water and dried. The material (3.08 g) was crystallized from hot 95% ethanol (50 ml) to give 2.56 g (70.6% yield) of methyl 3,5-dinitro-4-(4'-ethoxyphenoxy)benzoate. Melting point: 101°–103° C.

Mass spectrum (EI): M+ in high-resolution: calculated for $C_{16}H_{14}N_2O_8$: 362.075016; found, 362.074793 (deviation= 0.6 ppm).

1.2.2 Methyl 3,5-diiodo-4(4'-ethoxyphenoxy) benzoate

A portion (724.4 mg, 2.00 mmoles) of methyl 3,5-dinitro-4-(4'-ethoxyphenoxy)benzoate was dissolved in glacial acetic acid (50 ml), mixed with 10% palladium-on-carbon catalyst (Aldrich) (200 mg) in a Parr Model 4561 Mini-Reactor, charged with an atmosphere of $H_2$ (43 psi) and rapidly stirred at ambient temperature until the pressure-drop due to the reaction ceased (6 minutes, 16 psi final). The mixture was immediately filtered through a bed of celite to remove the catalyst and stripped of acetic acid solvent on a rotary evaporator to yield a brown, oily residue representing the crude 3,5-diamine derivative. The crude diamine was dissolved in glacial acetic acid (6.0 ml) and tetrazotized by adding it dropwise over a period of 3 minutes to a stirred, ice-cold solution of sodium nitrite (345 mg, 5 mmoles) in concentrated sulfuric acid (3.5 ml). After stirring for 30 minutes at ice-bath temperature, the viscous mixture was pipetted into a rapidly stirred solution of potassium iodide (3.0 g) in distilled water (2.5 ml) at ambient temperature. The dark mixture was stirred for 30 minutes and finally heated to 70° C. for 5 minutes. The mixture was poured into ethyl acetate (100 ml) and water (50 ml) was added. The two-phase mixture was transferred to a separatory funnel, additional ethyl acetate (50 ml) and water (50 ml) added, and the product extracted into the ethyl acetate. The organic (ethyl acetate) layer was washed with two additional portions of water (50 ml each) and dried over anhydrous sodium sulfate. Subsequent removal of ethyl acetate by evaporation yielded a dark, tarry residue.

This crude product was dissolved in acetone (8 ml) and purified by preparative thin-layer chromatography plates (five) (Whatman, silica-gel, 1000 µm layer, 20 cm×20 cm, with fluorescent indicator). The plates were developed in n-hexane:ethyl acetate:acetic acid (3:1:0.8 v/v/v). The product band ($R_f$=0.84), visualized under UV light, was collected from the respective plates, pooled, and eluted from the silica-gel (held in a sintered glass funnel) with ethyl acetate (3×50 ml). Removal of ethyl acetate yielded an off-white solid which was crystallized from 95% ethanol (10 ml). Yield: 275 mg total of two crops of white crystals (26% based on 2 mmoles of the dinitro precursor). Melting point: 123°–125° C.

Mass spectrum: EI, m/z (relative intensity): 524 (M+, 100), 496 (16.7), 310 (9.1), 242 (6.1), 211 (7.6), 155 (6.1). High-resolution data for the M+ peak: calculated for $C_{16}H_{14}I_2O_4$: 523.898163; found, 523.898737 (deviation=−1.1 ppm).

$^1$H NMR spectrum in DMSO-d$_6$ (δ(ppm) values relative to TMS): 1.303 (3H, triplet, J=6.94 Hz), 3.877 (3H, singlet), 3.971 (2H, quartet, J=6.95 Hz), 6.678 (2H, doublet, J=8.98 Hz, plus fine-splitting), 6.879 (2H, doublet, J=9.06 Hz, plus fine-splitting), 8.389 (2H, singlet).

1.3 Methyl 3,5-diiodo-4-(4'-n-propoxyphenoxy) benzoate (Compound 3)

Methyl 3,5-diiodo-4-(4'-n-propoxyphenoxy)benzoate (Compound 3) was prepared as described in Example 1.2. The dinitro precursor was synthesized by treating an aqueous solution of potassium 4-n-propoxy-phenolate (prepared from commercial 4-n-propoxy-phenol) with methyl 4-chloro-3,5-dinitrobenzoate. The dinitro product was reduced by $H_2$/Pd(C) to the diamine derivative, which was then tetrazotized with $NaNO_2/H_2SO_4$ and converted to the diiodo product by reaction with potassium iodide (Sandmeyer reaction). Purification was by preparative TLC and crystallization.

1.4 Methyl 3,5-diiodo-4-(4'-n-butoxyphenoxy) benzoate (Compound 4)

Methyl 3,5-diiodo-4-(4'-n-butoxyphenoxy)benzoate (Compound 4) was prepared as described in Example 1.2. The dinitro precursor was synthesized by treating an aqueous solution of potassium 4-n-butoxyphenolate (prepared from commercial 4-n-butoxyphenol) with methyl 4-chloro-3,5-dinitrobenzoate. The dinitro product was reduced by $H_2$/Pd(C) to the diamine derivative, which was then tetrazotized with $NaNO_2/H_2SO_4$ and converted to the diiodo product by reaction with potassium iodide (Sandmeyer reaction). Purification was by preparative TLC and crystallization.

1.5 Ethyl 3,5-diiodo-4-(4'-methoxyphenoxy) benzoate (Compound 5)

Ethyl 3,5-diiodo-4-(4'-methoxyphenoxy)benzoate (Compound 5) was synthesized by way of 3,5-diiodo-4-(4'-methoxyphenoxy)benzoyl chloride, the latter having been described in Borrows et al., 1949, *J. Chem. Soc.* 1949:

S185–S190. Thus, in a 10 ml flask 3,5-diiodo-4-(4'-methoxyphenoxy)benzoic acid (99.2 mg, 0.200 mmole) was converted to 3,5-diiodo-4-(4'-methoxyphenoxy)benzoyl chloride. After removal of excess thionyl chloride under vacuum, anhydrous ethanol (5.0 ml) was added with stirring and the mixture heated to 70° C. for 5 minutes. Excess ethanol was removed and the dry residue dissolved in hot 95% ethanol (4.0 ml), from which the product ester crystallized in the refrigerator (3° C.). Yield: 55.8 mg (53%) of buff-colored crystals. Melting point: 96°–98° C.

Mass spectrum (EI): High-resolution data for the M+ peak: calculated for $C_{16}H_{14}I_2O_4$, 523.898163; found, 523.898202 (deviation=–0.1 ppm).

$^1$H NMR spectrum in DMSO-$D_6$ ($\delta$(ppm) values relative to TMS): 1.336 (3H, triplet, J=7.19 Hz), 3.717 (3H, singlet), 4.336 (2H, quartet, J=7.06 Hz), 6.695 (2H, doublet, J=9.34 Hz, plus fine-splitting), 6.895 (2H, doublet, J=9.20, plus fine-splitting), 8.389 (2H, singlet).

1.6 3,5-diiodo-4-(4'-methoxyphenoxy)benzoic acid (Compound 6)

3,5-diiodo-4-(4'-methoxyphenoxy)benzoic acid (Compound 6) was synthesized as described in Borrows et al., 1949, *J. Chem. Soc.* 1949: S185–S190.

1.7 3,5-diiodo-4-(4'-methoxyphenoxy)benzamide (Compound 7)

3,5-diiodo-4-(4'-methoxyphenoxy)benzamide (Compound 7) was synthesized by amidating Compound 1. In a 125 ml flask, methyl 3,5-diiodo-4-(4'-methoxyphenoxy) benzoate (Compound 1) (100 mg, 0.196 mmole) was dissolved in anhydrous methanol (60 ml). Anhydrous ammonia gas was bubbled into the solution for 5 minutes at a moderate rate at ambient temperature. After standing for 1 hour in the stoppered flask, the ammonia gas treatment was repeated (5 minutes) and the mixture allow to stand in the stoppered flask for 48 hours. The methanol/ammonia was removed by rotary evaporation, the dry residue dissolved in methanol:water (7:3 v/v) (30 ml) and crystallized in the refrigerator (3° C.). Yield: 58.3 mg (60% yield) of buff-colored crystals. Melting point: 207°–209° C.

Mass spectrum (FAB): High-resolution data for the M+ peak: calculated for $C_{14}H_{11}I_2NO_3$, 494.882847; found, 494.881880 (deviation=2.0 ppm).

$^1$H NMR spectrum in DMSO-$d_6$ ($\delta$(ppm) values relative to TMS): 3.716 (3H, singlet), 6.682 (2H, doublet, J=8.93 Hz), 6.895 (2H, doublet, J=8.99 Hz), 7.528 (1H, singlet), 8.113 (1H, singlet), 8.402 (2H, singlet).

1.8 3,5-diiodo-4-(4'-methoxyphenoxy)-N-methyl benzamide (Compound 8)

3,5-diiodo-4-(4'-methoxyphenoxy)-N-methyl benzamide (Compound 8) was prepared by way of 3,5-diiodo-4-(4'-methoxyphenoxy)benzoyl chloride (see, Example 1.5). The acid chloride was reacted with excess methylamine in tetrahydrofuran at ambient temperature (1 hour), filtered to remove methylamine-hydrochloride precipitate, the solvent evaporated and the product crystallized from 95% ethanol.

1.9 3,5-diiodo-4-(4'-methoxyphenoxy)-N,N-dimethyl benzamide (Compound 9)

3,5-diiodo-4-(4'-methoxyphenoxy)-N,N-dimethyl benzamide (Compound 9) was prepared way of 3,5-diiodo-4-(4'-methoxyphenoxy)benzoyl chloride (see, Example 1.5). The acid chloride was reacted with excess dimethylamine in tetrahydrofuran at ambient temperature (1 hour), filtered to remove dimethylamine-hydrochloride precipitate, the solvent evaporated and the product crystallized from absolute ethanol.

1.10 Methyl 3,5-diiodo-4-(4'-hydroxyphenoxy) benzoate (Compound 10)

Methyl 3,5-diiodo-4-(4'-hydroxyphenoxy) benzoate (Compound 10) was prepared as described in Example 1.2. The dinitro precursor was prepared by reacting 4-chloro-3,5-dinitrobenzoate with hydroquinone in pyridine solution as described in Borrows et al., 1949, "The Synthesis of Thyroxine Related Substances. Part II. The Preparation of Dinitrodiphenyl Ethers," *J. Chem. Soc.* 1949 (Supp. Issue No. 1):S190–S199.

1.11 Methyl 3,5-diiodo-4-phenoxybenzoate (Compound 11)

Methyl 3,5-diiodo-4-phenoxybenzoate (Compound 11) was prepared as described in Example 1.2. The dinitro precursor was synthesized by treating an aqueous solution of potassium phenolate (prepared from commercial phenol) with methyl 4-chloro-3,5-dinitrobenzoate. The dinitro product was reduced by $H_2$/Pd(C) to the diamine derivative, which was then tetrazotized with $NaNO_2/H_2SO_4$ and converted to the diiodo product by reaction with potassium iodide (Sandmeyer reaction). Purification was by preparative TLC and crystallization.

1.12 Methyl 3,5-diiodo-4-(4'-iodophenoxy)benzoate (Compound 12)

Methyl 3,5-diiodo-4-(4'-iodophenoxy)benzoate (Compound 12) was synthesized as described in Example 1.2. Since the iodo-substituent in the dinitro precursor is itself labile with respect to reduction by $H_2$/Pd(C), the iodo-dinitro precursor was reduced to the iodo-diamine with iron powder in acetic acid/95% ethanol (see, e.g., Gemmill et al., 1956, "3-Iodo-, 3,3'-Diiodo- and 3,3,'-Diiodo-5-bromothyroxine," *J. Am. Chem. Soc.* 78:2434–2436). The iodo-diamine was then tetrazotized and converted to the triiodo product using the Sandmeyer reaction. After purification by preparative TLC, the product (m.p. 139°–141° C.) was crystallized from ethanol.

Mass spectrum (EI): High resolution data for the M$^+$ peak: calculated for $C_{14}H_9O_3I_3$, 605.768600; found, 605.767839 (deviation=1.3 ppm).

$^1$H NMR spectrum in DMSO-$d_6$ ($\delta$(ppm) values relative to TMS): 3.879 (3H, singlet), 6.628 (2H, doublet, J=8.97 Hz plus fine-splitting), 7.670 (2H, doublet, J=9.12 Hz plus fine-splitting), 8.396 (2H, singlet).

1.13 Methyl 3,5-diiodo-4-(3'-methoxyphenoxy) benzoate (Compound 13)

Methyl 3,5-diiodo-4-(3'-methoxyphenoxy)benzoate (Compound 13) was synthesized as described in Example 1.2. The dinitro precursor was synthesized by treating an aqueous solution of potassium 3-methoxy phenolate (prepared from commercial 3-methoxyphenol) with methyl 4-chloro-3,5-dinitrobenzoate. The dinitro product was reduced by $H_2$/Pd(C) to the diamine derivative, which was then tetrazotized with $NaNO_2/H_2SO_4$ and converted to the diiodo product by reaction with potassium iodide (Sandmeyer reaction). Purification was by preparative TLC and crystallization.

1.14 Methyl 3,5-diiodo-4-(2'-chloro-4'-methoxyphenoxy)benzoate (Compound 14)

Methyl 3,5-diiodo-4-(2'-chloro-4'-methoxyphenoxy) benzoate (Compound 14) was synthesized by the general methodology described in Example 1.2, but with an alternate method for the reduction of the dinitro precursor.

1.14.1 Methyl 3,5-dinitro-4-(2'-chloro-4'-methoxyphenoxy)benzoate

The dinitro precursor was prepared by reacting 2-chloro-4-methoxyphenol (Aldrich Chemical Co., Milwaukee, Wis.) as the potassium 2-chloro-4-methoxyphenolate with methyl 4-chloro-3,5-dinitrobenzoate, as described in Example 1.2.1. The methyl 3,5-dinitro-4-(2'-chloro-4'-methoxyphenoxy)benzoate product (66% yield) was crystallized from ethanol to give orange crystals. Melting point: 116°–119° C.

Mass Spectrum (EI): $M^+$ in high resolution: calculated for $C_{15}H_{11}ClN_2O_8$, 382.020393; found, 382.020187 (deviation=0.5 ppm).

1.14.2 Methyl 3,5-diiodo-4-(2'-chloro-4'-methoxyphenoxy)benzoate

Since the 2'-chloro substituent in the dinitro precursor is labile with respect to reduction by $H_2/Pd(C)$, the precursor was reduced to the 2'-chloro diamine with iron powder in acetic acid/95% ethanol, similarly to Example 1.12. Thus, in a 250 mL flask methyl 3,5-dinitro-4-(2'-chloro-4'-methoxyphenoxy)benzoate (765.5 mg, 2.00 mmol) was dissolved in glacial acetic acid (35 mL) and 95% ethanol (35 mL), the solution heated to 70° C. and iron powder added (2.00 g). The mixture was vigorously swirled in a heating bath (70° C.). After 3 min. of swirling, the mixture developed a brown color. Swirling was continued at 70° C. for 35 min. The mixture was then transferred to a separatory funnel, water (250 mL) and ethyl acetate (250 mL) were added, the product extracted into the ethyl acetate layer, and the ethyl acetate phase allowed to separate from the aqueous phase (3 hours). The extract was dried over anhydrous $Na_2SO_4$, filtered and the ethyl acetate removed by rotary evaporation to yield the crude 3,5-diamino product, which solidified.

The crude diamino product was immediately dissolved in glacial acetic acid (6.0 mL), tetrazotized and converted via the Sandmeyer reaction to methyl 3,5-diiodo-4-(2'-chloro-4'-methoxyphenoxy)benzoate as described in Example 1.2. After purification by preparative thin layer chromatography ($R_f$=0.70) as described in Example 1.2, the product was crystallized from 95% ethanol (250.8 mg off-white crystals, 23% yield). Melting point: 132°–134° C.

Mass spectrum: EI, m/z (relative intensity): 546 (34), 545 (16), 544 ($M^+$, 100), 418 (6), 382 (6). High resolution data for the $M^+$ peak: calculated for $C_{15}H_{11}ClI_2O_4$, 543.843541; found, 543.843424 (deviation=0.2 ppm).

$^1$H NMR spectrum in DMSO-$D_6$ ($\delta$(ppm) values relative to TMS): 3.747 (3H, singlet), 3.881 (3H, singlet), 6.328 (1H, doublet, J=8.97 Hz), 6.780 (1H, doublet of doublets, J=9.10 Hz and J=2.95 Hz), 7.195 (1H, doublet, J=3.02 Hz), 8.400 (2H, singlet).

1.15 Other Compounds

Additional thyroxine analogues described herein can be synthesized using the above-described syntheses from appropriate starting materials, as will be readily apparent to those having skill in the art of organic chemistry. Additional guidance can be found in the art, particularly in Borrows et al., 1949, "The Synthesis of Thyroxine and Related Substances. Part I. The Preparation of Tyrosine and Some of its Derivatives, and a New Route to Thyroxine," *J. Chem. Soc.* 1949 (Supp. Issue No. 1): S185–S190; Borrows et al., 1949, "The Synthesis of Thyroxine and Related Substances. Part II. Preparation of Dinitrophenyl Ethers," *J. Chem. Soc.* 1949 (Supp. Issue No. 1) :S190–S199; Clayton et al., 1951, "The Synthesis of Thyroxine and Related Substances. Part VIII. The Preparation of Some Halogeno- and Nitro-diphenyl Ethers," *J. Chem. Soc.* 1951:2467–2473; Gemmill et al., 1956, "3-Iodo-, 3,3'-Diiodo- and 3,3'-Diiodo-5-bromothyroxine," *J. Am. Chem. Soc.* 78:2434–2436; Meltzer et al., 1957, "Thyroxine Analogs," *J. Org. Chem.* 22:1577–1581; Crowder et al., 1958, "Bisbenzylisoquinolines. Part II. The Synthesis of 5-(2-Aminoethyl)-4'-carboxy-2,3-dimethoxydiphenyl Ether," *J. Chem. Soc.* 1958:2142–2149; Jorgensen, 1978, "Thyroid Hormones and Analogues. I. Synthesis, Physical Properties and Theoretical Calculations" In: *Hormonal Proteins and Peptides* Vol. VI, pp. 57–105, C. H. Li, Ed., Academic Press, NY (and references cited therein); and Jorgensen, 1978, "Thyroid Hormones and Analogues. II. Structure-Activity Relationships," In: *Hormonal Proteins and Peptides*, Vol. VI, pp. 107–204, C. H. Li, Ed., Academic Press, NY (and references cited therein).

EXAMPLE 2

ACTIVATION OF PURIFIED PROTEIN PHOSPHATASE 2A

Compounds 1 and 3, as identified in Table 1, were tested for protein phosphatase 2A activation.

2.1 Preparation of $^{32}$P-labeled Histone H1 Substrate

Histone H1 was phosphorylated with protein kinase C (Upstate Biotechnology, Inc., Lake Placid, N.Y.) in a volume of 100 μL according to standard protocols. Alternatively, histone H1 was phosphorylated with p34cdc2 kinase purified from rapidly multiplying Mytilus Edulis embryos at 4–8 stage after isolation with the $P^{13}$-Suc agarose technique (Smythe and Newport, 1992, "Coupling of Mitosis to the Completion of S Phase in Xenopus Occurs via Modulation of the Tyrosine Kinase that Phosphorylates p34cdc2," *Cell* 68:787–797).

2.2 Phosphatase Assay 125 ng purified protein phosphatase 2A (Upstate Biotechnology, Inc., Lake Placid, N.Y.; Usui et al., 1983, *J. Biol. Chem.* 258:10455–10463) was preincubated with thyroxine analogue (50 μM) in buffer (20 mM MOPS or Tris, pH 7.5, 1 mM $MgCl_2$, 60 μM β-mercaptoethanol) for 10 min. at 23° C. Total reaction volume was 20 μL. $^{32}$P-labeled histone H1 substrate (10 μg, $10^5$ cpm) was added and the dephosphorylation reaction allowed to proceed for 5 min. at 23° C., after which time the reaction was quenched by addition of 2 μL Laemmli buffer. An identical reaction containing 125 ng untreated protein phosphatase 2A was run as a control.

Phosphorylated and dephosphorylated histone H1 were separated by gel electrophoresis (12% SDS-PAGE), bands containing phosphorylated histone H1 excised and assayed for $^{32}$P activity via scintillation counter. The cpm in Table 2 represents the loss of $^{32}$P from histone-$^{32}$P.

2.3 Results

The velocity of dephosphorylation in 5 min. is an indication of the initial velocity ($V_{init}$) of the dephosphorylation reaction. $V_{init}$ for compounds 1 and 3 is provided in Table 2, below.

TABLE 2

| Activation of Protein Phosphatase 2A | |
|---|---|
| Thyroxine Analogue | Activity/5 min (cpm) |
| Control | 10217 ± 1708 |
| Compound 1 | 24655 ± 8600 |
| Compound 3 | 7521 ± 1562 |

Reported values are the average of three samples.

These results show that a short (10 min.) preincubation of protein phosphatase 2A with DIME (Compound 1) more than doubles $V_{init}$ of histone H1 dephosphorylation. The 4'-propoxy homologue did not activate protein phoshatase 2A. These data indicate that even minor changes in the ends of the DIME pharmacophore structure (i.e. the methoxy and methyl ester groups) significantly affect activity. These data correlate strongly with protein phosphatase 2A activation observed in in vitro malignant cell assays (see Example 3) and with in vivo anti-tumorigenic efficacy as observed in mice (see Examples 4 and 6).

EXAMPLE 3

ACTIVATION OF PROTEIN PHOSPHATASE A2 IN TUMOR CELL CULTURES

Compounds 1–13 were tested for protein phosphatase 2A activation in malignant tumor cell cultures in vitro according to the protocol described in Bauer et al., 1996, "Modification of Growth Related Enzymatic Pathways and Apparent Loss of Tumorigenicity of a Ras-Transformed Bovine Endothelial Cell Line by Treatment with 5-Iodo-6-Amino-1,2-Benzopyrone (INH$_2$BP)," International J. of Oncology 8:239–252. The results for activation by DIME (Compound 1) are tabulated in Table 3. All other compounds were ineffective.

TABLE 3

| Effect of DIME of the Phosphatase Activity of E-ras 20 and DU-145 Cell Nuclear Extracts | |
|---|---|
| | Phosphatase Activity (fmol Pi/mg protein × min.) |
| E-ras nuclear extract (5–10 μg protein per assay) | 29 ± 5 |
| E-ras nuclear extract ± 50 μM DIME | 44 ± 7 |
| DU-145 (5–10 μg protein per assay) | 12.1 ± 3 |
| DU-145 + 50 μM DIME | 19.1 ± 2.5 |

Pi = inorganic phosphate

These results demonstrate that 50 μM DIME activates protein phosphatase 2A by at least two-fold in both E-ras transformed bovine endothelial cells and DU-145 cells.

EXAMPLE 4

CYTOCIDAL ACTION ON HUMAN CANCER CELLS

The cytocidal action of Compounds 1–13 was tested on seven human cancer cell lines in vitro. DIME (Compound 1) was maximally active, with the ethoxy derivative (Compound 2) having 25–30% maximal activity.

4.1 Experimental Protocol

Seven human cancer cell lines were obtained from the American Tissue Culture Collection (Rockville, Md.) and maintained in the recommended growth media. Cells were seeded into wells (2 cm$^2$) at a density of 2×10$^4$ cells/cm$^2$. Various concentrations of Compounds 1–13 were added to the media at the time of seeding.

The cultures were incubated for 72 hours at 37° C. (5% CO$_2$ atmosphere). Following incubation, cells were detached with trypsin and counted in a hemocytometer.

4.2 Results

DIME (Compound 1) was maximally active, with the ethoxy analogue (Compound 2) having 25–30% maximal activity. All other analogues tested (Compounds 3–13) were completely inactive.

The experimental results for DIME (Compound 1) are tabulated in Table 4, below. $I_{100}$ designates the concentration at which no viable cells remained; $I_{50}$ the concentration at which 50% viable cells remained, as compared to a control.

TABLE 4

| Effect of DIME on Various Human Cancer Cell Lines | | |
|---|---|---|
| Cell Line | $I_{50}$ (μM) | $I_{100}$ (μM) |
| HT 144 (melanoma) | 0.5 | 4.0 |
| DU 145 (prostate cancer) | 0.5 | 3.5 |
| HeLA (cervical cancer) | 0.6 | 3.5 |
| HL-60 (promyelocytic leukemia) | 0.6 | 3.0 |
| MDA-MD-231 (mammary cancer) | 0.4 | 3.0 |
| SK-Br-3 (mammary cancer) | 0.6 | 5.0 |
| T47D (ductal mammary cancer) | 0.7 | 3.5 |

EXAMPLE 5

INHIBITION OF TUMOR CELL GROWTH

Compounds 1 and 14 were tested for inhibition on the growth of MDA-MD-231 cancer cells. Compound 14 exhibited about 25% inhibitory activity as compared to DIME (Compound 1).

5.1 Experimental Protocol

MDA-MD-231 human cancer cells were obtained from the American Tissue Culture Collection (Rockville, Md.) and maintained in the recommended growth media. Cells were grown in the presence of various concentrations of Compounds 1 and 14 for 3 days at 37° C.

5.2 Results

The experimental results are tabulated in Table 5, below.

TABLE 5

| Growth Rate of MDA-MD-231 Cells | | | |
|---|---|---|---|
| compound 1 (μM) | Cells (× 10$^6$) | Compound 14 | Cells (× 10$^6$) |
| 0.0 | 0.95 | 0.0 | 0.95 |
| 0.5 | 0.20 | 0.5 | 0.95 |
| 1.0 | 0.10 | 1.0 | 0.71 |
| 2.0 | 0.09 | 2.0 | 0.20 |

The 2'-chloro analogue of DIME (Compound 14) exhibited about 25% inhibitory activity as compared to DIME (Compound 1).

EXAMPLE 6

LOSS OF TUMORIGENICITY OF E-RAS TRANSFORMED BOVINE ENDOTHELIAL CELLS

The morphologic action of DIME (Compound 1) was tested in a highly tumorigenic E-ras transformed bovine endothelial cell line.

6.1 Experimental Protocol

E-ras transformed bovine endothelial cells (Bauer et al., 1996, *Intl. J. Oncology* 8:239–252) were exposed to 10 µM DIME for 3 days. The DIME-treated cells ($10^5$ or $10^6$ cells/100 µL) were injected subcutaneously into nude mice and tumor progression followed for 25 days.

6.2 Results

As illustrated in FIG. 1, exposure of E-ras transformed endothelial cells to 10 µM DIME for a period of 3 days induced extensive micronucleation, coinciding with a loss of tumorigenicity. As illustrated in FIG. 2, animals exposed to non-treated cells exhibited tumor growth (top curves), succumbing to tumors at 25 days. Exposure of cells to 10 µM DIME prior to injection nearly completely abolished tumorigenicity (lower curves). Tumors did not appear even after 3 months without in vivo drug treatment.

EXAMPLE 7

IN VIVO EXPERIMENTS

The following examples demonstrate the non-toxicity, bioavailability, serum half-life ($t_{1/2}$) and in vivo efficacy of DIME in treating human mammary cancer xenografts in mice.

7.1 Toxicity

Ten nude mice were administered a daily oral dose of $^{14}$C-labeled DIME (Compound 1) (1.0 g/kg, 0.1 mL in corn oil) for a period of 12–15 days. No ill effects were observed in any of the mice during the entire time of treatment.

7.2 Serum Half-Life (t½) and Bioavailability

Mice were orally dosed with 126 mg/kg $^{14}$C-labeled DIME (Compound 1). After dosing, blood sampling times were 15 and 30 minutes and 1, 2, 4, 6, 8 and 24 hours. Aliquots (50 µL) of blood were assayed in a liquid scintillation counter and data expressed as microgram-equivalents per mL. The blood level data were analyzed by the RSTRIP method (Micromath, Salt Lake City, Utah).

Parallel groups of mice were dosed intravenously with 24.5 mg/kg $^{14}$C-labeled DIME and blood sampling times were 10, 20 and 30 minutes and 1, 2, 4, 6 and 8 hours.

7.2.1 Results

The blood serum levels of $^{14}$C-labeled DIME (mg-eq./ml) are illustrated in FIG. 3. The area under the blood concentration-time curve was 665.28 µg-hr./mL for the oral route (data represented by circles) and 156 µg-hr/mL for the intravenous route (data represented by squares). Bioavailability of orally administered DIME was calculated to be 83% from these data using a standard ratio×dose method. DIME half-life (t½) was about 2–2.5 hours.

7.3 In Vivo Efficacy

The ability of human tumors to grow as xenografts in athymic mice (e.g., nude mice) provides a useful in vivo model for studying the biological response to therapies for human tumors. Since the first successful xenotransplantation of human tumors into athymic mice (Rygaard and Povlsen, 1969, *Acta Pathol. Microbiol. Scand.* 77:758–760), many different human tumor cell lines (e.g., mammary, lung, genitourinary, gastrointestinal, head and neck, glioblastoma, bone and malignant melanomas) have been successfully transplanted and grown into nude mice. Human mammary tumor cell lines, including MCF-7, ZR75-1 and MDA-MB-231, have been established as subcutaneous grafts in nude mice (Warri et al., 1991, *Intl. J. Cancer* 49:616–23; Ozzello & Sordat, 1980, "Behaviour of Tumors Produced by Transplantation of Human Mammary Cell Lines in Athymic Nude Mice," *Eur. J. Cancer* 16:553–559; Osbourne et al., 1985, *Cancer Res.* 45:584–590; Siebert et al., 1983, *Cancer Res.* 43:2223–2239).

This experiment demonstrates inhibition of MDA-MB-231 xenografts in nude mice.

7.3.1 Experimental Protocol

MDA-MB-231 (human mammary cancer) cells were obtained from American Type Culture Collection (Rockville, Md.) and maintained in the recommended growth media. Twenty nude mice were each inoculated subcutaneously with MDA-MB-231 cells ($10^6$ cells/100 µL). To one group of ten mice, DIME was administered by gavage (250 mg/kg, 10 mL/kg in corn oil) once per day, 5 days per week, for a total of 32 days. The other (control) group of ten mice was given administered vehicle only according to the same dosing schedule. Tumors were measured twice weekly using a Vernier caliper, and the mean tumor volume was determined at each time point. Comparisons between groups were made using an unpaired, two-tailed t-test and the results were analyzed using analysis of variance.

7.3.2 Results

The average tumor mass at days 14, 21, 28 and 32 post-inoculation for treated and untreated mice is tabulated in Table 6.

TABLE 6

| MDA-MB-231 Tumor Volume After DIME Treatment | | | | |
|---|---|---|---|---|
| Treatment group | Day 14 ± SEM[a] (p value) | Day 21 ± SEM[a] (p value) | Day 28 ± SEM[a] (p value) | Day 32 ± SEM[a] (p value) |
| Control (vehicle) | 284.6 ± 42.0 | 622.2 ± 58.1 | 979.0 ± 154 | 1176.6 ± 222.4 |
| DIME (250 mg/kg) | 172.0 ± 34.3 (p = 0.06) | 285.7 ± 62.4 (p = 0.02) | 430 ± 85.6 (p = 0.01) | 543.8 ± 122.1 (p = 0.01) |
| % decrease | 40% | 54% | 56% | 54% |

[a]SEM = standard error of the mean

These data indicate that DIME effects significant reduction of malignant tumor growth, even under a non-optimized treatment regimen.

7.4 In Vivo Efficacy

Other thyroxine analogues described herein are tested as described above. The analogues are expected to exhibit activity according to these assays.

EXAMPLE 8

FORMULATIONS

The following examples provide exemplary, not limiting, formulations for administering the thyroxine analogues of the invention to mammalian, especially human, patients. While the examples demonstrate formulations of DIME, it is to be understood that any of the thyroxine analogues described herein may be formulated as provided in the following examples.

8.1 Tablet Formulation

Tablets each containing 60 mg of active ingredient are made up as follows:

| | |
|---|---|
| DIME | 60 mg |
| Starch | 45 mg |
| Microcrystalline Cellulose | 45 mg |
| Sodium carboxymethyl starch | 4.5 mg |

| | |
|---|---|
| Talc | 1 mg |
| Polyvinylpyrrolidone (10% in water) | 4 mg |
| Magnesium Stearate | 0.5 mg |
| | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules are dried at 50°–60° C. and passed through a No. 18 mesh U.S. sieve. The sodium carboxymethyl starch, magnesium stearate and talc, previously passed through a No. 60 mesh U.S. sieve, are then added to the granules, which, after mixing are compressed by a tablet machine to yield tablets each weighing 150 mg.

Tablets can be prepared from the ingredients listed in Table 1 by wet granulation followed by compression.

8.2 Gelatin Capsules

Hard gelatin capsules are prepared using the following ingredients:

| | |
|---|---|
| DIME | 250 mg/capsule |
| Starch dried | 200 mg/capsule |
| Magnesium Stearate | 10 mg/capsule |

The above ingredients are mixed and filled into hard gelatin capsules in 460 mg quantities.

8.3 Aerosol Solution

An aerosol solution is prepared containing the following components:

| | |
|---|---|
| DIME | 0.25% (w/w) |
| Ethanol | 29.75% (w/w) |
| Propellant 22 (Chlorodifluoromethane) | 77.00% (w/w) |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

8.4 Suppositories

Suppositories each containing 225 mg of active ingredient are made as follows:

| | |
|---|---|
| DIME | 225 mg |
| Saturated fatty acid glycerides | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

8.5 Suspensions

Suspensions each containing 50 mg of medicament per 5 mL dose are made as follows:

| | |
|---|---|
| DIME | 50 mg |
| Sodium carboxymethylcellulose | 50 mg |
| Syrup | 1.25 mL |
| Benzoic acid solution | 0.10 mL |
| Flavor | q.v. |
| Color | q.v. |
| Purified water to | 5 mL |

The active ingredient is passed through a No. 45 mesh U.S. sieve and mixed with the sodium carboxymethyl cellulose and syrup to form a smooth paste. The benzoic acid solution, flavor and some color are diluted with some of the water and added, with stirring. Sufficient water is then added to produce the required volume.

The foregoing written specification is considered to be sufficient to enable one skilled in the art to practice the invention. Various modifications of the above-described modes for carrying out the invention which are obvious to those skilled in the pharmaceutical arts or related fields are intended to be within the scope of the following claims.

What is claimed is:

1. A method for treating a malignant tumor in a mammal comprising the step of administering an amount of methyl 3,5-diiodo-4-(4'-methoxyphenoxy) benzoate sufficient to depress growth of the malignant tumor.

2. The method of claim 1 wherein said malignant tumor is selected from the group consisting of melanoma, prostate cancer, cervical cancer, promyelocytic leukemia, mammary cancer, and ductal mammary cancer.

3. The method of claim 1 wherein said malignant tumor is selected from the group consisting of mammary cancer and ductal mammary cancer.

* * * * *